United States Patent
List

(10) Patent No.: US 11,583,632 B2
(45) Date of Patent: Feb. 21, 2023

(54) AMBULATORY INFUSION DEVICE

(71) Applicant: Roche Diabetes Care, Inc., Indianapolis, IN (US)

(72) Inventor: Hans List, Oberzent (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 193 days.

(21) Appl. No.: 16/431,992

(22) Filed: Jun. 5, 2019

(65) Prior Publication Data

US 2019/0290845 A1  Sep. 26, 2019

Related U.S. Application Data

(63) Continuation of application No. PCT/EP2017/082617, filed on Dec. 13, 2017.

(30) Foreign Application Priority Data

Dec. 14, 2016 (EP) .................................... 16204056

(51) Int. Cl.
*A61M 5/178* (2006.01)
*A61M 5/142* (2006.01)
(Continued)

(52) U.S. Cl.
CPC ........ *A61M 5/1782* (2013.01); *A61M 5/1452* (2013.01); *A61M 5/14216* (2013.01);
(Continued)

(58) Field of Classification Search
CPC ............ A61M 5/1782; A61M 5/14216; A61M 5/14244; A61M 5/1452; A61M 5/3146;
(Continued)

(56) References Cited

U.S. PATENT DOCUMENTS

2004/0237793 A1* 12/2004 Zurcher .................. G07F 13/10
99/275
2005/0238503 A1* 10/2005 Rush ................. A61M 5/14244
417/322
(Continued)

FOREIGN PATENT DOCUMENTS

DE  3515624 A1  11/1986
EP  1970677 A1  9/2008
(Continued)

OTHER PUBLICATIONS

European Patent Application No. 16173361.3, Valve Drive Unit with Shape Memory Alloy Actuator, Filed Jun. 7, 2016, Roche Diabetes Care GmbH et al., 47 pages.
International Search Report and Written Opinion, PCT/EP2017/082617, dated Mar. 19, 2018, 20 pages.

*Primary Examiner* — Bhisma Mehta
*Assistant Examiner* — Nidah Hussain
(74) *Attorney, Agent, or Firm* — Bose McKinney & Evans LLP

(57) ABSTRACT

An ambulatory infusion device including a pump drive unit, a valve drive unit and a control unit. The pump drive unit includes a pump actuator and a pump driver coupled to a piston of a metering pump unit. The valve drive unit includes a valve actuator and a valve driver coupled to a valve unit for transmitting a valve switching force or torque. The control unit controls a repeated execution of: (a) placing the valve unit in a filling state; (b) displacing the piston in a retraction direction; (c) displacing the piston in an advancing direction by a backlash compensation distance; (d) switching the valve unit from the filling state into a draining state; and (e) further displacing the piston in the advancing direction in a number of incremental steps over an extended time period.

16 Claims, 2 Drawing Sheets

(51) Int. Cl.
*A61M 5/145* (2006.01)
*A61M 5/31* (2006.01)
*A61M 5/315* (2006.01)
*A61M 39/22* (2006.01)
*A61M 5/14* (2006.01)
*A61M 5/168* (2006.01)

(52) U.S. Cl.
CPC ...... *A61M 5/14244* (2013.01); *A61M 5/3146* (2013.01); *A61M 5/31575* (2013.01); *A61M 5/31578* (2013.01); *A61M 5/31583* (2013.01); *A61M 39/22* (2013.01); *A61M 5/1413* (2013.01); *A61M 5/16809* (2013.01); *A61M 2039/226* (2013.01); *A61M 2205/0266* (2013.01)

(58) Field of Classification Search
CPC .......... A61M 5/31575; A61M 5/31578; A61M 5/31583; A61M 39/22; A61M 5/1413; A61M 5/16809; A61M 2039/226; A61M 2205/0266; A61M 2005/14252; A61M 2005/14256; A61M 2005/1426; A61M 2005/14264; A61M 2005/14268; A61M 2005/14272; A61M 5/14276; A61M 5/1428; A61M 2005/14284; A61M 2005/14288; A61M 5/145; A61M 2005/14506; A61M 2005/14513; A61M 5/14526; A61M 5/14248; A61M 2005/14292
USPC ....................................................... 604/506
See application file for complete search history.

(56) References Cited

U.S. PATENT DOCUMENTS

| | | | |
|---|---|---|---|
| 2007/0215235 A1* | 9/2007 | Ranalletta | B65B 3/003 141/2 |
| 2013/0245604 A1* | 9/2013 | Kouyoumjian | A61M 5/1408 604/506 |
| 2014/0039392 A1* | 2/2014 | Geipel | A61M 5/365 604/152 |
| 2016/0015904 A1* | 1/2016 | Plumptre | A61M 5/3146 604/211 |
| 2019/0083706 A1* | 3/2019 | List | F16K 1/221 |

FOREIGN PATENT DOCUMENTS

| | | | | |
|---|---|---|---|---|
| EP | 2329857 A1 | 6/2011 | | |
| EP | 2361646 A1 | 8/2011 | | |
| EP | 2482900 B1 | 4/2015 | | |
| EP | 2881128 A1 | 6/2015 | | |
| EP | 2921189 A1 | 9/2015 | | |
| EP | 2921189 A1 * | 9/2015 | ............. | A61M 5/36 |
| WO | WO 2009/039214 A2 | 3/2009 | | |
| WO | WO-2009041826 A1 * | 4/2009 | ........ | A61M 5/16827 |
| WO | WO 2012/065780 A2 | 5/2012 | | |
| WO | WO 2012/140052 A1 | 10/2012 | | |
| WO | WO 2012/140063 A1 | 10/2012 | | |
| WO | WO 2013/030000 A1 | 3/2013 | | |
| WO | WO-2014139918 A1 * | 9/2014 | ........ | A61M 5/31585 |
| WO | WO 2015/082305 A1 | 6/2015 | | |
| WO | WO-2015082305 A1 * | 6/2015 | ........ | A61M 5/16809 |
| WO | WO 2017/211711 A1 | 12/2017 | | |

* cited by examiner

AMBULATORY INFUSION DEVICE

CROSS REFERENCE TO RELATED APPLICATIONS

This application is a continuation of PCT/EP2017/082617 filed Dec. 13, 2017 which claims priority from EP 16 204 056.2 filed on Dec. 14, 2016 the entire disclosures of both of which are hereby incorporated herein by reference.

BACKGROUND

The present disclosure relates to the field of ambulatory infusion devices and ambulatory infusion systems for infusing a liquid drug into a patient's body over an extended time period. A typical field of application is the therapy of Diabetes Mellitus via Continuous Subcutaneous Insulin Infusion (CSII).

Ambulatory infusion devices are well known in the art, for example in the therapy of Diabetes Mellitus by Continuous Subcutaneous Insulin Infusion (CSII) as well as in pain therapy or cancer therapy, and are available from a number of suppliers, such as Roche Diabetes Care GmbH, Germany, or Medtronic MiniMed Inc., Calif., USA.

According to a classic and well-established design, those ambulatory infusion devices or systems are typically of the syringe-driver type. A number of drawbacks of such devices are known in the art. In particular, they have a limited precision because they involve delivering very small drug amounts, typically in the nanoliter range, out of a drug cartridge having an overall drug volume in the milliliter range. Therefore, additional concepts and architectures have been proposed which use a dedicated dosing unit downstream from the drug reservoir. The dosing unit may comprise, e.g., a micro membrane pump or a micro piston pump, and is adapted to couple to a drug reservoir and is especially designed for precise metering of small volumes. While several designs for such dosing units are known in the art, they are rather complex, most of them are expensive and/or critical with respect to large scale manufacture.

In one example, EP1970677 discloses a system with a miniaturized metering piston pump with a dosing cylinder that is repeatedly coupled to and filled from a larger reservoir, followed by coupling the dosing cylinder to an infusion site and infusing the liquid drug out of the dosing cylinder in incremental steps and over an extended time period. For alternatively coupling the dosing cylinder to the reservoir and the infusion site, a valve system is proposed.

An ambulatory infusion system in accordance with the principles disclosed in EP1970677 has the advantage that the metering is carried out from a comparatively small reservoir (the dosing cylinder) of substantially smaller cross-sectional area as compared to, e. g., a standard syringe driver as explained before. Based on a similar piston displacement precision, a significantly higher dosing accuracy may principally be achieved. Also, the influence of other factors that may reduce the dosing accuracy, e. g. thermal expansion, is significantly reduced. A drawback of this approach, however is the need for regular refilling the dosing cylinder from the drug container. In typical diabetes therapy applications one filling of the dosing cylinder may, in dependence on the patient, nutrition, etc. last for between a day or more and only a number of hours, or even less.

Each refilling of the dosing cylinder, however, involves reversals of the piston displacement direction. A backlash, resulting from generally present play of the pump drive chain (in particular, the reduction gear and spindle drive for the rotatory-to-linear transformation) occurs whenever the driving direction of the pump drive, and, consequently, the displacement direction of the piston, is reversed. The backlash has the effect that, upon reversal of the driving direction, the piston is not displaced in accordance with the drive actuation until the backlash is compensated for. The requirement for repeatedly reversing the driving direction that is inherent to the overall architecture may considerably reduce the high basic accuracy that is in principle achievable and may, in dependence of the overall design, outweigh the advantages.

EP2361646 proposes avoiding the backlash in a dosing unit according to the disclosure of disclosed in EP1970677 by mechanical biasing of the threaded spindle. Similarly, the WO2013030000 discloses a biasing device that ensures biasing independent of the motion direction.

SUMMARY

The present disclosure provides improvements in the situation regarding the accuracy of an ambulatory infusion system with a dosing unit and in particular to reduce or avoid imprecisions resulting from backlash. Favorably, the disadvantages of known systems are either fully or partly avoided.

According to an aspect of the disclosure, improvements can be achieved with an ambulatory infusion device. The ambulatory infusion device includes a pump drive unit. The pump drive unit includes a pump actuator and a pump driver that is coupled to the pump actuator. The pump driver is designed for coupling to a piston of a metering pump unit for transmitting a pump driving force and/or pump driving torque from the pump actuator to the piston. The ambulatory infusion device further includes a valve drive unit. The valve drive unit includes a valve actuator and a valve driver that is coupled to the valve actuator. The valve driver is designed for coupling to a valve unit for transmitting a valve switching force and/or valve switching torque from the valve actuator to the valve unit. The ambulatory infusion device further includes a control unit. The control unit is configured to control a repeated execution of a sequence of:

(a) operating the valve actuator to switch the valve unit into a filling state;

(b) operating the pump actuator to displace the piston in a retraction direction;

(c) operating the pump actuator to displace the piston into an advancing direction, the advancing direction being opposite to the retraction direction, by a backlash compensation distance;

(d) operating the valve actuator to switch the valve unit from the filling state into a draining state;

(e) operating the pump actuator to further displace the piston in the advancing direction in a number of incremental steps over an extended time period.

The repeated sequence of steps (a), (b), (c), (d), (e) reflects the regular operation of the ambulatory infusion system. It is assumed that the ambulatory infusion system is initialized and primed, e. g., the fluidic path from the drug reservoir to the dosing unit and further to the infusion site is filled with liquid drug, favorably, with no or only a negligible amount of gas/air.

The expression "metering pump unit" relates to a pump unit that is designed and suited for the metered administration of well-defined liquid amounts substantially independent of further conditions of the fluidic system, in particular pressure. The metering is achieved by controlled displacement of the piston inside the dosing cylinder, in particular inside a blind-hole shaped metering cavity, similar to a syringe. The basic principles of a dosing unit that is assumed in the following are disclosed in EP1970677 to which reference is made regarding the principle design and properties of a dosing unit.

The expression "ambulatory infusion device" refers to a device that includes the piston drive unit, the valve drive unit, and the control unit. The expression "ambulatory infusion system" refers to a combination of an ambulatory infusion device with fluidic components, in particular a dosing unit and potentially further components such as a container and an infusion line, in an operational configuration.

A movement of the piston in the retraction direction results in the liquid-filled inner volume of the dosing cylinder being increased. The expression "inner volume of the dosing cylinder" refers to the liquid-filled volume, i. e., a volume that is delimited by the piston, an adjacent front wall of the dosing cylinder, and a circumferential inner wall of the dosing cylinder which also defines a sealing and sliding surface for the piston. By a piston movement into the retraction direction, the dosing cylinder is accordingly filled by sucking liquid drug from the container into the dosing cylinder in a syringe-like way. Similarly, a piston movement in the advancement direction results in the liquid-filled inner volume of the dosing cylinder being decreased, thereby administering or more generally expelling liquid drug out of the dosing cylinder. The advancement direction and the retraction direction are opposite linear directions. The displacement movement of the piston in the retraction direction in step (b) ends in a retracted piston position. The advancement movement of the piston in the advancement direction in step (e) ends in an advanced piston position. When repeatedly executing a sequence of steps (a) to (e) as defined above, the piston starts the retraction movement in step (b) in the advanced piston position. Similarly, the piston starts the advancement movement of steps (c), (e) in the retracted piston position.

In a sequence of the before-defined steps, the dosing cylinder is filled with liquid drug in step (b) as a filling step and is emptied in step (e) as an administering step where the liquid drug is administered out of the dosing cylinder in a controlled and metered way. At the end of the filling step, the piston assumes the retracted piston position and at the end of the administering step the piston assumes the advanced piston position. In a typical embodiment, the control unit controls the pump drive to carry out the filling step in a comparatively short time period of, e.g., 15 seconds to 45 seconds. The administering step is, in contrast, carried out over an extended time period in accordance with the user's therapeutic requirements, over a time period of, e.g., some hours up to a day or even more. The time delay between the increments and/or the incremental displacement may further be equal or vary. Further aspects of the administration are explained further below in the context of exemplary embodiments.

Repeatedly carrying out a sequence of steps (a), (b), (d), (e) is, in principle, known. A backlash occurs at the beginning of steps (b) and (e), i.e., at the beginning of the piston movement in the retraction or advancement direction, respectively. The backlash at the beginning of step (e) is more critical because liquid drug is administered to the patient in step (e).

In accordance with the present disclosure, the backlash is not reduced and favorably avoided by way of mechanical means, such as biasing. Instead, the backlash is generally accepted, but its disadvantageous influence on the dosing accuracy in step (e) is avoided by adding step (c) as backlash compensation step. In step (c), the piston is displaced by the backlash compensation distance while the dosing cylinder is fluidically coupled with the container, before switching the valve unit into the draining state in step (d). Liquid drug is accordingly expelled out of the dosing cylinder and back into the container.

The expression "backlash compensation distance" refers to the distance by which the pump drive is controlled to displace the piston. It is the distance by which the piston, respectively its hard core as explained below, would be displaced by the pump drive if the backlash was zero, i.e., no backlash was in fact present. The actual piston displacement is smaller than the backlash compensation distance because some backlash does occur. The backlash compensation distance is favorably selected such that the piston displacement corresponds to the maximum backlash that may occur, favorably including a safety margin for coping with the piston elasticity. In a typical design, the piston has a piston core that is generally made from a hard material, typically plastics, with a circumferential soft sealing. In addition to the backlash that results from drive chain tolerances, the friction between the piston sealing and the inner wall of the dosing cylinder may cause, in combination with the elasticity of the piston sealing, a deviation between the desired liquid displacement in accordance with the movement of the piston core, and the actual liquid displacement out of the dosing cylinder. The safety margin is favorably chosen such that the elastic deformation of the sealing that occurs after reversal of the piston direction takes place during the backlash compensation. At the end of backlash compensation step (c), the backlash and the piston sealing elasticity are accordingly compensated. In the administration step (e), the piston will accordingly be displaced in accordance with the drive actuation beginning with the initial displacement.

To execute a sequence of steps (a) to (e), the present disclosure is based on the use of a dosing unit that allows valve switching independent of the piston movement. Such a dosing unit is disclosed, e.g., in EP1970677 and in particular embodiments in European Patent Application 16173361.3 and WO2015/082305.

The engagement of the pump driver and the pump driver coupler is bidirectional in the sense that force and/or torque may be transmitted in opposing directions. The pump drive unit is reversible.

The valve unit of a dosing unit may be designed in a cyclic way such that the valve state switches between the filling state and the draining state each time the valve drive is actuated, while the valve driving force and/or valve driving torque is always applied in the same direction. In such embodiments the valve drive unit may be designed for a single driving direction and the coupling between the valve driver and the valve driver coupler may be designed for force/torque transmission in a single direction. Alternatively, however, the valve unit may be designed such that the valve drive direction is reversed for switching into the filling state and the draining state, respectively. In such embodiments, the valve drive unit is reversible and the engagement of the pump driver and the pump driver coupler is bidirectional in the sense that force and/or torque may be transmitted in opposing directions.

In particular where reference is made to components of an ambulatory infusion device, a dosing unit or an ambulatory infusion system, the piston advancement direction may also referred to as "proximal direction" and the piston retraction direction may be referred to as "distal direction".

In one embodiment, the backlash compensation distance is between 0.3 mm and 1 mm. As explained before, the actual piston displacement distance is smaller than the backlash compensation distance and is in a typical range of some tenths of a millimeter, e.g., 0.1 mm to 0.5 mm.

In an embodiment, the control unit is configured to start a sequence of step (a) to (e) in an advanced piston stop position. The advanced piston stop position is a piston position beyond which the piston is not further displaced in the advancement direction and corresponds to a minimum filling volume of the dosing cylinder in operation. For such embodiments, the advanced piston stop position is the advanced piston position as explained before. The advanced piston stop position may in principle be defined by a mechanical advancement stop of the pump drive unit and/or the pump unit, e.g., when the piston hits the ground of the metering cavity. In a particularly favorable embodiment, however, the advanced piston stop position is slightly, e.g., some hundredths of a millimeter, distant from the mechanical stop in the advancement direction. During an initialization of the dosing unit, the piston may be displaced into the advancement direction until it hits the mechanical stop, which is detected and stored by the control unit. During subsequent operation and in particular during execution of the sequence with steps (a) to (e), piston movement into the advancement direction stops in the advanced piston stop position before reaching the mechanical stop. The piston assuming the advanced piston stop position is favorably detected by the control unit.

In an embodiment, the control unit is configured, in step (b), to stop operating the pump actuator upon the piston assuming a retracted piston stop position. The retracted piston stop position is a piston position beyond which the piston is not further displaced in the retraction direction and corresponds to a maximum filling volume of the dosing cylinder in operation. For such embodiments, the retracted piston stop position is the retracted piston position as explained before. An ultimate limit for the retracted piston stop position is a piston position where further piston displacement into the retraction direction would result in the piston leaving the metering cavity, the engagement between piston and dosing cylinder becoming untight, or the piston hitting a mechanical stop. In a particularly favorable embodiment, however, the retracted piston stop position is slightly, e. g. some hundredths of a millimeter, distant from such limit in the advancement direction. The piston assuming the retracted piston stop position is favorably detected by the control unit.

An embodiment with an advanced piston stop position and a retracted piston stop position that are not defined by mechanical stops is favorable in so far as the piston never hits, after initialization and during regular operation, a mechanical stop, which would unavoidably reduce the dosing accuracy.

In an embodiment where the piston movement ends in the retracted piston stop position, the full available travel range of the piston is used. In filling step (b), the dosing cylinder is filled to its maximum available filling volume, and in the administering step (e) the dosing cylinder is completely or substantially completely emptied.

The pump drive unit may be designed as a rotatory drive or a linear displacement drive. If the pump drive unit is a rotatory drive, the movement that is carried out by the pump driver during operation is purely rotational. If the pump drive unit is a linear displacement drive, the movement that is carried out by the pump driver during operation is a pure linear displacement movement or a combined displacement and rotational movement.

Generally, a rotational movement of the pump actuator (typically a rotational motor) is transformed into a displacement movement via the interaction of a threaded spindle and a corresponding nut, or, more generally, an outer-threaded element and a corresponding inner-threaded element.

In the following text, the case of the pump drive unit being designed as a rotatory drive is discussed first. Either of the inner-threaded or the corresponding outer-threaded element may receive the driving torque from the pump actuator and carry out a rotational movement, while the other of the threaded spindle and the nut may carry out a pure linear displacement movement or a combined displacement and rotational movement.

Further, the transformation from a pure rotational movement into a displacement movement may carried out by the drive unit, the dosing unit, or at the interaction of the pump driver as part of the drive unit and the pump driver coupler as part of the dosing unit.

The pump driver may be formed by a drive nut that is driven by the pump actuator. In such an embodiment, the pump driver coupler of the dosing unit can be realized by a threaded spindle that is favorably prevented from rotating by an anti-rotation arrangement as generally known. An end of the threaded spindle is coupled with the piston or is formed integrally with the piston, such that the displacement movement is transmitted to the piston.

Further, for the pump drive unit being designed as a rotatory drive, the pump driver may be a rotatable threaded spindle that is driven by the pump actuator and the pump driver coupler may be a corresponding inner-threaded element, respectively nut element, that is coupled with the piston or formed integrally with the piston. The inner-threaded element may be prevented from rotation by an anti-rotation arrangement that may be part of the ambulatory infusion device or the dosing unit.

Further, for the pump drive unit being designed as a rotatory drive, the pump driver may be an unthreaded rotating element that transmits, in an engaged configuration, a driving torque but no linear force to the pump driver coupler. The pump driver may be especially formed as a rotating elongated element with a non-circular, e.g., quadratic or hexagonal cross section, e.g., as pin of non-circular (e. g. hexagonal, square or rectangular) cross section, or have an opening of such cross section, axially with the axis of rotation. In this case, the valve driver coupler has a corresponding non-circular cross section to engage the valve driver in rotationally coupled and axially sliding engagement. The valve driver coupler may, for example, have the form of an elongated pin of non-circular cross section and extend in distal direction from a threaded spindle and in coaxial alignment with the threaded spindle, and optionally be formed integral with the threaded spindle. In a further variant, the threaded spindle has, at least in a distal section, a non-circular cross section to engage the valve driver. For the rotational-to-linear transformation, an inner threaded element, respectively nut, is provided in this embodiment in engagement with the threaded spindle. The inner-threaded element may be part of the ambulatory infusion device or the dosing unit, and be realized, e.g., by a distal section of the dosing cylinder. For the here-described type of embodiment, the threaded spindle, respectively outer-threaded element, carries out a screw-like movement as combined linear displacement movement and rotational movement.

An embodiment where the nut, respectively inner-threaded element, is provided as part of the dosing unit is particularly favorable, because the loop of forces is closed in a short manner within the dosing unit, independent from other elements of the ambulatory infusion device, in particular the housing and movable parts of the pump drive chain. Further, if the threaded spindle is rigidly attached to or formed integral with the piston, the movement that is carried out by the piston upon activation of the pump drive is a screw-like, i.e., a combined rotatory and displacement movement, rather than a pure displacement movement. While the total amount of frictional losses between the piston and the inner wall of the dosing cylinder are avoided, thereby preventing slip-stick effects, the dosing precision is accordingly increased.

In the following text, the alternative case of the pump drive unit being designed as a linear displacement drive is discussed. For such embodiments, the pump coupler and the pump coupler driver generally execute identical linear displacement movements that are parallel to each other and have identical displacement distances. The pump driver and the piston may be designed for direct coupling engagement, with the pump driver coupler being favorably integral with the piston or rigidly coupled to the piston. The engagement between the pump driver and the pump driver coupler may be a typical releasable push-pull engagement.

In an embodiment, the valve driver includes a meshing pin for meshing engagement with a valve driver coupler of the valve unit. Examples of a valve driver are disclosed in European Patent Application 16173361.3 the disclosure of which is hereby incorporated by reference herein. A meshing pin as valve driver is favorable in that it is comparatively simple in design and enables a simple and reliable engagement that is typically releasable.

In an embodiment, the valve driver is a driver element of a step switching mechanism, in particular, a Geneva wheel mechanism. A step switching mechanism has the characteristics that it transforms a continuous input movement into a discontinuous output movement such that an output element of the step switching mechanism changes from an initial state to a final state discontinuously. The output-versus-input characteristic is step-like. In the present context, the input element of the step switching mechanism is the valve driver, and the output element of the step switching mechanism is the valve driver coupler, with the initial state (before actuation) being either and the final state being the other of the filling state and the draining state, respectively. In the present context, a step switching mechanism has the particular advantage that it allows well-defined valve switching without requiring precise and complex control of the valve drive. Further, the step switching mechanism may be designed in a way that allows simple and generally releasable coupling between valve driver and valve driver coupler without requiring precise relative-pre-alignment. Particular embodiments of valve drive units, in particular valve drivers, and corresponding dosing units, in particular valve drive couplers, are disclosed in the WO2015/082305, to the disclosure of which is hereby incorporated by reference herein.

In an embodiment, the valve actuator includes either of a stepper motor and a Shape Memory Alloy (SMA) actuator. Both stepper motors and SMA actuators are particularly suited for use as, or in, a valve actuator because they have comparatively low costs and allow a simple and reliable valve drive design. Particular designs for a valve drive unit with two SMA wires are disclosed in the before-mentioned European Patent Application 16173361.3. Particular designs for a valve drive unit with a stepper motor and a step-switching mechanism are disclosed in the before-mentioned WO2015/082305. In alternative embodiments, however, other types of actuators, such as an electromagnetic actuator or a standard DC motor, may be used as well.

In an embodiment, the control unit is configured to detect if the piston is in a retracted piston stop position or an advanced piston stop position. For this purpose, the control unit may be configured to determine the piston position indirectly, e.g., via a rotatory encoder of the pump drive. Alternatively, or additionally, end switches, e.g., optical or electromechanical end switches, or a piston position sensor, e.g., according to the WO2012/140052 may be provided for this purpose.

It is noted that for spindle-based pump drives, a fixed relation exists, via the thread pitch, between the rotatory actuator movement and the displacement movement of the pump driver, provided the backlash is compensated for. Therefore, it is sufficient to detect at least one of the retracted and the advanced plunger stop position or any other well-defined position as reference position, and the control unit may be configured to determine, starting from the reference position, the current piston position by counting actuation increments of the pump actuator. Actuation increments in the form of the smallest incremental movement or displacement that may be realized, may, e.g., be determined via a rotational drive shaft encoder of a motor.

In an embodiment, the ambulatory infusion device is designed for releasable coupling with the dosing unit via a coupling movement.

The coupling movement may, e.g., be or include a linear relative displacement movement. The coupling typically includes inserting the dosing unit into a dosing unit compartment of the ambulatory infusion device or attaching the dosing unit to the ambulatory infusion device. When coupling the ambulatory infusion device with the dosing unit, an engagement of the pump driver with the pump driver coupler and/or an engagement of the valve driver with the valve driver coupler may be established automatically. Alternatively, such coupling may be established afterwards by corresponding drive actuations.

In an embodiment, the valve drive unit is designed to stay out of engagement with the valve unit during the coupling movement. In particular, the valve driver of the valve drive unit stays out of engagement with the valve driver coupler of the drive unit. Instead, the engagement is only established afterwards by a corresponding valve drive actuation. This type of embodiment has the particular advantage that no precise alignment is required during the coupling. Embodiments are disclosed, e.g., in the before-mentioned WO2012/140052. Alternatively, a dosing unit and/or the ambulatory infusion device may include corresponding alignment members that align the valve driver and the valve driver coupler during the coupling. Embodiments are disclosed, e.g., in the before-mentioned European Patent Application 16173361.3.

According to a further aspect, an ambulatory infusion system is provided. The ambulatory infusion system includes an ambulatory infusion device. The ambulatory infusion system further includes a dosing unit. The dosing unit includes a metering pump unit. The pump unit includes a dosing cylinder, a piston and a valve unit. The piston is arranged inside the dosing cylinder in a sealing and displaceable manner and is displaceable between a retracted piston stop position and an advanced piston stop position. The dosing unit further includes a valve unit. The valve unit has a filling port, the filling port being designed for fluidic coupling with a liquid drug reservoir. The valve unit further has a draining port, the draining port being designed for fluidic coupling with an infusion site interface. The valve unit further has a shut-off body, the shut-off body being movable between a filling position where it fluidically couples the filling port with the dosing cylinder and an alternative draining position where it fluidically couples the dosing cylinder with the draining port. The dosing unit further has a pump driver coupler and a valve driver coupler. The pump driver coupler is coupled to or integral with the piston and the valve driver coupler is coupled to or integral with the shut-off body. The valve drive unit is in engagement with the valve driver coupler and the piston driver is in engagement with the piston. In operation, the piston driver coupler receives the pump driving force and/or pump driving torque from the pump driver, and the valve driver coupler receives the valve switching force and/or valve switching torque from the valve driver. The valve driver coupler is part of the valve unit and the pump driver coupler is part of the pump unit. The pump unit, in particular the dosing cylinder, and the valve unit, are typically designed as a compact fluidic device.

Further aspects of the dosing unit are explained above and below in the context of cooperation between a dosing unit and an ambulatory infusion device. The ambulatory infusion system may further include a drug reservoir and/or an infusion site interface, such as an infusion cannula, and an infusion line or tubing that fluidically couples draining port with the infusion site interface.

According to a further aspect, a backlash compensation method for a dosing unit for liquid drug infusion is provided. The method includes repeatedly executing a sequence of:

(a) switching a valve unit into a filling state;

(b) displacing a piston in a retraction direction into a retracted piston position;

(c) displacing the piston into an advancing direction, the advancing direction being opposite to the retraction direction, by a backlash compensation distance;

(d) switching the valve unit from the filling state into a draining state;

(e) further displacing the piston in the advancing direction in a number of incremental steps over an extended time period to an advanced piston position.

The method may be carried out with a dosing unit wherein the dosing unit includes a metering pump unit. The pump unit includes a dosing cylinder, a piston and a valve unit. The piston is arranged inside the dosing cylinder in a sealing and displaceable manner and is displaceable between a retracted piston stop position and an advanced piston stop position. The dosing unit further includes a valve unit. The valve unit has a filling port, the filling port being designed for fluidic coupling with a liquid drug reservoir. The valve unit further has a draining port, the draining port being designed for fluidic coupling with an infusion site interface. The valve unit further has a shut-off body, the shut-off body being movable between a filling position where it fluidically couples the filling port with the dosing cylinder and an alternative draining position where it fluidically couples the dosing cylinder with the draining port.

The method may further include, prior to the carrying out the before-mentioned repeated sequence with steps (a)-(e), fluidically coupling the filling port with the liquid drug reservoir and favorably maintaining the coupling while repeatedly carrying out the sequence with steps (a)-(e).

The method may, in particular, be carried out with a dosing unit, an ambulatory infusion device and/or an ambulatory infusion system in accordance with any embodiment of such dosing unit, ambulatory infusion device and/or ambulatory infusion system described herein. Corresponding embodiments of dosing units, ambulatory infusion devices and ambulatory infusion systems accordingly disclose, at the same time, corresponding method embodiments.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein.

Figure 1:
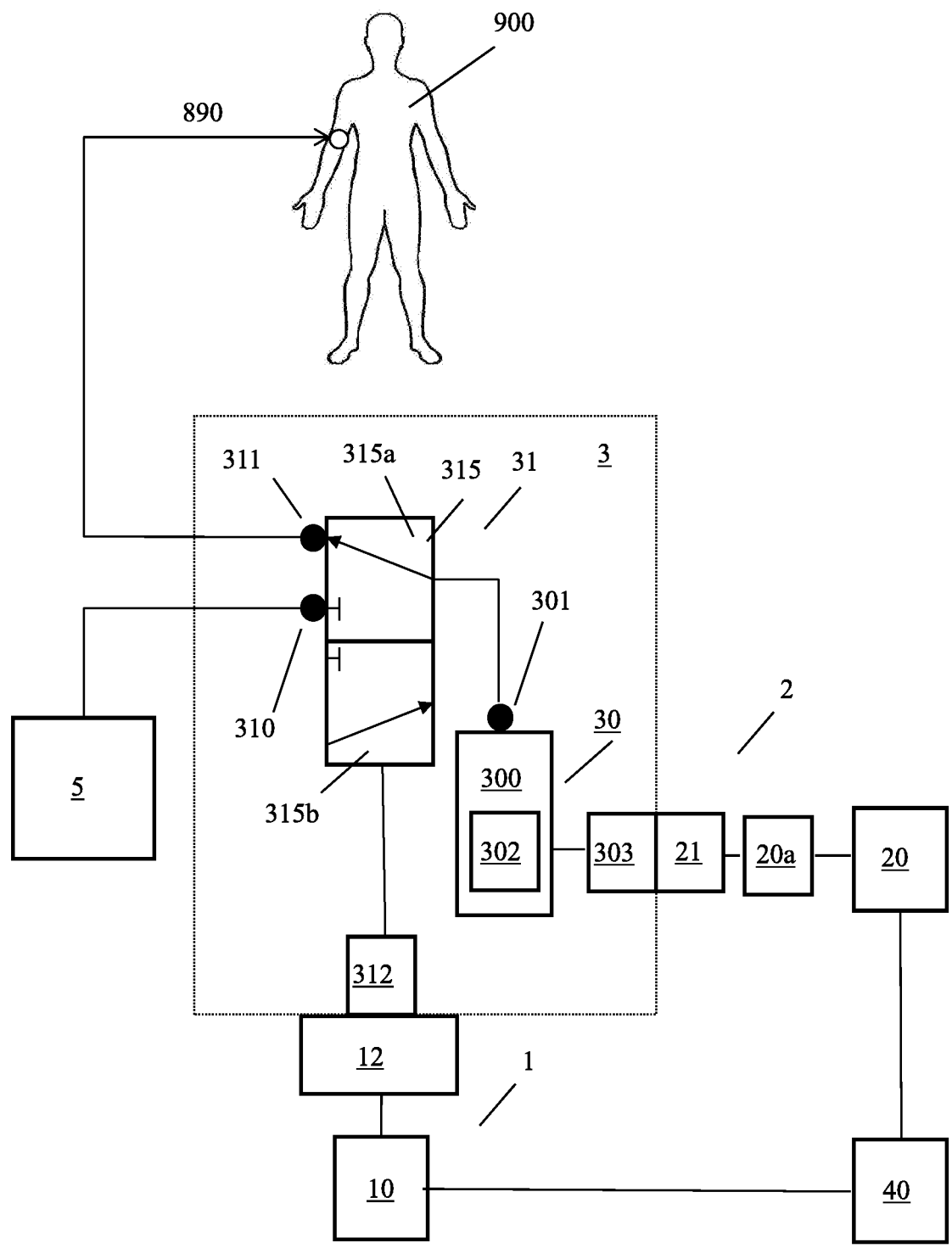
FIG. 1 schematically shows an ambulatory infusion system in accordance with the present disclosure.

Corresponding reference characters indicate corresponding parts throughout the several views. Although the exemplification set out herein illustrates embodiments of the invention, in several forms, the embodiments disclosed are not intended to be exhaustive or to be construed as limiting the scope of the invention to the precise forms disclosed.

DETAILED DESCRIPTION

Reference is first made to FIG. 1. FIG. 1 shows functional units of an ambulatory infusion device and ambulatory infusion system in accordance with the present disclosure.

The ambulatory infusion system includes a dosing unit 3, and an ambulatory infusion device with a pump drive unit 2 and a valve drive unit 1. The ambulatory infusion device further includes an electronic control unit 40. The ambulatory infusion system further includes, in an operational state, a liquid drug reservoir 5. It is to be noted that only those structural and functional units are shown that are of particular relevance in view of the present disclosure. Other units, such as power supply, user interface etc. are typically present as well.

The dosing unit 3 includes a metering pump unit 30 (also referred to as pump unit) and a valve unit 31. The metering unit 30 includes a dosing cylinder 300 and a piston 302 that is arranged inside of the dosing cylinder 300 in a sealing and displaceable manner, similar to a syringe. In a proximal front wall of the dosing cylinder 300, a bore is arranged as pump port 301 that fluidically couples the inner volume of the dosing cylinder 300 with the valve unit 31.

The valve unit 31 includes a shutoff body 315 that is movable between a filling position 315b and a draining position 315a. If the shutoff body is in the filling position, the valve unit is referred to as being in a filling state. Likewise, if the shutoff body 315 is in the draining position, the valve unit 31 is referred to as being in the draining state. During operation, the valve unit 31 is repeatedly switched between the filling state and the draining state as further discussed below. The reservoir 5 is fluidically coupled to the valve unit 31 via a filling port 310. A patient 900 is fluidically coupled to the valve unit 31 via a draining port 311 and an infusion site interface 890. It is noted that the infusion site interface 890 is exemplarily shown as integral with an infusion line, e.g., a catheter. Alternatively, the infusion pump device may be designed as a patch pump that is directly attached to a patient's body, e.g., via an adhesive pad. Here, the infusion site interface is represented by a cannula.

The valve unit 31 includes a shutoff body 315 that is arranged in a valve bearing in a sealing and rotatable manner.

The shutoff body 315 includes a flow channel arrangement that realizes, in dependence of a rotational position of the shutout body 315, either the filling state 315b or the draining state 315a, respectively. The valve unit 31 is typically arranged in line with and proximal from the pump unit 30. In a typical arrangement that is also assumed in the following, the shutoff body axis is parallel to and optionally coincides with a longitudinal axis of the dosing cylinder 300 along which the piston 302 is displaced. This arrangement, however, is not essential.

The dosing unit 3 further includes, as part of the valve unit 31, a valve driver coupler 312 for switching the valve unit 31 between the filling position, 315b, and the draining position 315a. Similarly, the dosing unit 3 includes, as part of the metering pump unit 30, a pump driver coupler 303 for displacing the piston 302 inside the dosing cylinder 300 as explained before. The pump driver coupler 303 may be fully or partly integral with the piston 302.

The operation of the metering unit 30 and the valve unit 31 is independent from each other. That is, the piston 302 may be displaced inside the dosing cylinder 300 without affecting the state of the valve unit 31. Likewise, the state of the valve unit 31 may be changed, respectively switched, without affecting the position of the piston 302 inside the dosing cylinder 300. Further, a valve switching between the filling state and the draining state does not involve a liquid displacement between the filling port 310 and the draining port 311, resulting from the movement of the shutoff body 315. Consequently, a valve switching does not involve the dosing of liquid to the patient. This aspect is of particular relevance because the controlled and metered dosing is carried out exclusively by controlled displacement of the piston 302. For highly concentrated drugs such as typical liquid insulin formulations, an unintended drug administration that may result from the valve switching may cause undesired and potentially severe medical complications.

In a typical arrangement, the dosing unit 3 with the metering pump unit 30 and the valve unit 31 is formed as a compact device and in an integral way. Therefore, the pump port 301 is, in contrast to the filling port 310 and the draining port 311, not accessible from outside the dosing unit 3. In a typical embodiment, the dosing cylinder has an inner diameter in a range of 3 mm to 5 mm, and the travel distance of the piston 302 is in a range of 5 mm to 15 mm.

Figure 2:
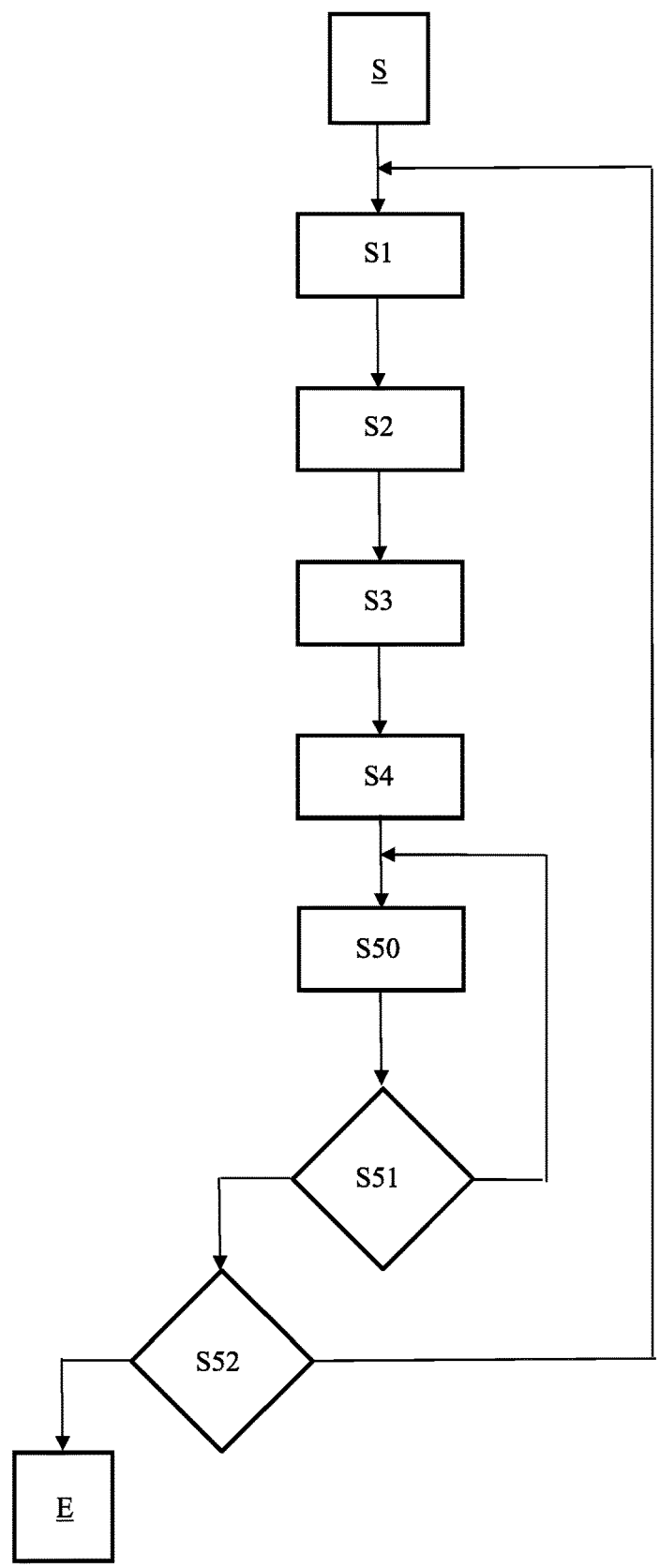
FIG. 2 schematically illustrates the operational flow of a sequence in accordance with the present disclosure.

With respect to the valve unit 31, it is further noted that FIG. 2 only shows the states 315a, 315b where either of the filling port 310 or the draining port 311 is coupled to the pump port 301. In a further intermediate state, however, all three ports 301, 310, 311 are closed, resulting in fluidic isolation. In a typical embodiment and mode of operation, however, such intermediate state is only assumed during switching operations for a negligible transient period.

The pump drive unit 2 includes the pump driver 21 that is designed to releasably engage the pump driver coupler 303 for displacing the piston inside the dosing cylinder 300 as explained before in both the advancement direction and the retraction direction. The pump drive unit 2 further includes a pump actuator 20 that typically includes a motor, e.g., a standard DC motor, a stepper motor or electronically commutated respectively brushless DC motor. The pump drive unit 2 further includes a gear 20a with a reduction gear and a rotatory-to-linear transformation gear, in particular a spindle drive or screw drive, that transforms a rotary actuator movement into a reversible linear displacement movement of the pump driver 21, and, via the pump driver coupler 303, of the piston 302. The pump driver 21 may be realized as plunger. The pump driver coupler 303 may be firmly attached to or integrated into a distal portion of the piston 302. The pump driver 21 and the pump driver coupler 303 are designed for push-pull-coupling, e.g., as bayonet coupling, snap-fit coupling, or the like. A reciprocal movement of the pump driver 21 results in a corresponding reciprocal piston movement in proximal or distal direction, respectively. Alternatively, the pump driver 21 is realized as drive nut or threaded spindle, and the pump driver coupler is respectively realized as threaded spindle or drive nut.

The valve drive unit 1 includes a valve actuator 10 and a valve driver 12 that is designed for coupling with the valve driver coupler 312. Exemplary embodiments of the valve drive unit 1 and the valve driver coupler 312 are disclosed in European Patent Application 16173361.3 and WO2015/082305 the disclosures of which are incorporated herein by reference.

The control unit 40 controls the overall operation of the ambulatory infusion device and ambulatory infusion system and in particular the valve actuator 10 and the pump actuator 20. The control unit 40 typically includes one or more microcomputers and/or microcontrollers with corresponding computer program code, respectively firmware, for controlling operation of the ambulatory infusion system. The control unit 40 typically further includes peripheral circuitry as known in the art.

The pump drive unit 2, the valve drive unit 1 and the control circuitry 40 typically belong to an ambulatory infusion device as a common compact device. The ambulatory infusion device is designed for an extended lifetime of a number of months, e.g., six months, or even a number of years, while the dosing unit 3 and the reservoir 5 are disposable and of substantially shorter lifetime of typically a number of days up to, e.g., two weeks, in dependence of the patient's individual drug needs. The valve driver 12 and the pump driver 21 of the ambulatory infusion device, as well as the pump driver coupler 303 and the valve driver coupler 312 of the dosing unit 3 are therefore designed for releasable coupling in the sense that coupling as explained before between the pump driver 21 and the pump driver coupler 303, respectively between the valve driver 12 and the valve driver coupler 312 can be released without damaging the pump driver 21 and the valve driver 12. Alternatively, however, the ambulatory infusion system may, including the dosing unit 3, the pump drive unit 2 and the valve drive unit 1, be realized as fully integral unit for an application time. In this case, releasable coupling as explained before may not be required and the coupling may be non-releasable instead.

FIG. 2 illustrates an operation flow that may be executed by an ambulatory infusion device and ambulatory infusion system according to FIG. 1. The single steps are carried out under control of the control unit 40.

The operational flow as shown in FIG. 2 reflects the regular operation of the ambulatory infusion system which is assumed to be initialized and primed, as explained before.

While not being essential, it is first assumed that the piston 302 is at the beginning in the advanced piston stop position, and the liquid-filled volume of the dosing cylinder is accordingly minimal, typically negligible. Further, it is assumed that the valve unit 31 is in the draining state. Further it is assumed that the whole fluidic system, including the infusion line 890 with the infusion site interface, is primed, i.e., filled with liquid drug. Some amount of gas, in particular air, may, however be present in some embodiments.

The operational flow starts in step S. In a step S1, the valve actuator 10 is operated to switch the valve unit 31 into the filling state, thereby fluidic coupling the dosing cylinder 30 with the reservoir 5.

In a subsequent step S2, the pump actuator 20 is operated to move the pump driver 21, and accordingly the piston 302, into the retraction direction and into a retracted piston position, thereby increasing the volume between the piston 302 and the pump port 301. Because of the fluidic coupling with the reservoir 5, liquid drug is accordingly sucked into the dosing cylinder 300. In principle, the piston 302 may be moved by any desired distance (up to a design-given maximum displacement distance), thereby filling the dosing cylinder 300 with a desired liquid volume. For the sake of simplicity, it may be assumed that the piston 302 is moved into the retracted piston stop position, i.e., the dosing cylinder 300 is filled to its maximum available filling volume. This, however, is not essential.

In a subsequent step S3, the pump actuator 20 is operated to move the pump driver 21, and accordingly the piston 302, into the advancing direction by a backlash compensation distance. As compared to preceding step S2, the operational direction of the pump drive unit 2 is reversed. Since the state of the valve unit 31 is not changed between steps S2 and S3, the dosing cylinder 300 is, in step S3, still fluidically coupled with the drug reservoir 5. In step S3, liquid drug is accordingly displaced out of the dosing cylinder 300 back into the liquid drug reservoir 5.

In principle, the volume that is displaced out of the dosing cylinder 300 (for a piston displacement into the advancement direction) or sucked into the dosing cylinder 300 (for a piston displacement into the retraction direction) is given by the product of the displacement distance and the inner cross section area of the dosing cylinder 300. Precise dosing is accordingly possible by controlling the piston displacement. The drive chain of the ambulatory infusion system, including the pump actuator 20, the gear 20a, the pump driver 21, the pump driver coupler 303 and the piston 302, typically has some unavoidable play and accordingly (reversal) backlash, substantive part of which is typically caused by the rotatory-to-linear transformation gear. This backlash needs to be overcome and the elasticity of the typically present piston seal needs to be overcome each time the displacement direction is reversed, before the piston 302 is displaced in accordance with the drive actuation and dosing can be carried out with the required precision. Via step S3, this happens while the dosing cylinder 300 is coupled with the reservoir 5. The backlash compensation distance is selected to correspond to the backlash plus a safety margin in order to cope with the elastic deformation of the piston seal, as explained before. The liquid drug volume that is displaced in step S3 back into the reservoir 5 is accordingly somewhat smaller that would be expected from the backlash compensation distance, with the difference being caused by the backlash.

In subsequent step S4, the valve actuator 10 is operated to switch the valve unit 31 into the draining state, thereby fluidically coupling the dosing cylinder 300 with the infusion line 890 and the infusion site interface. Steps S1, S2, S3, S4 form, in combination, a filling routine, respectively refilling routine, for the dosing cylinder 300.

In subsequent step S50, the plunger 302 is displaced by an incremental step or incremental distance in the advancement direction. Since the valve unit 31 is in the draining state, a corresponding incremental liquid drug amount is accordingly displaced out of the dosing cylinder 300 and administered to the patient 900. Since the backlash has been compensated for in preceding step S3, the administration is carried out with high precision. The liquid drug administration in step S50 may be a patient-commanded bolus administration or an incremental basal administration. Incremental basal administrations are carried out under control of the control unit 40 substantially continuously in accordance with a normally time-varying, e.g., circadian basal administration schedule. For example, an incremental basal administration is carried out with a fixed time interval of, e.g., three minutes. Alternatively, a fixed incremental basal administration volume of, e.g., 0.05 IU (International Units) or U. I. may be administered with each incremental basal administration, and the time interval may be varied in accordance with the basal administration schedule.

In subsequent step S51, it is determined whether the remaining filling volume of the dosing cylinder 300 is above a refilling threshold and the operational flow branches in dependence of the result. In the affirmative case, the operational flow returns to step S50 and a next basal or bolus administration may be carried out. It is noted that the next drug administration is typically not carried out immediately, but after lapse of the time interval as explained before, or as bolus administration at any time on demand. Since the drive direction is not reversed between the incremental drug administrations, no backlash is present.

The refilling threshold may be zero or substantially zero. In this case, the dosing cylinder 300 is fully emptied until the piston 302 is in the design-given advanced piston stop position where it cannot be further advanced, as explained before. Alternatively, however, the refilling threshold may be somewhat larger.

In the negative case in step S51, the remaining filling volume of the dosing cylinder 300 is low and the operational flow moves to step S52. In step S52, it is determined whether the remaining filling level of the reservoir 5 is sufficient for refilling the dosing cylinder 300 and the operational flow branches in dependence of the result.

In the affirmative case in step S52, the operational flow proceeds with step S1 as explained before, and the dosing cylinder 300 is refilled with liquid drug. In the negative case in step S52, the reservoir 5 (and potentially the dosing unit 3) and the operational flow ends in step E. A corresponding indication is favorably provided to the patient and a reservoir change routine or a disposable change routine (not shown) may be initiated.

The operational flow shown in FIG. 2 corresponds to a basic embodiment and may be modified in a number of ways.

For example, a simple threshold compensation is used in step S51 in order to determine whether the dosing cylinder 300 should be refilled before the next following administration. In an alternative, the dosing cylinder 300 is fully or substantially emptied, even if the remaining filling volume of the dosing cylinder 300 is smaller than the liquid drug amount that shall be administered. The remaining amount (that cannot be administered before refilling) may be stored by the control unit 40 as carry-forward. Subsequent to the re-filling of the dosing cylinder with steps S1, S2, S3, S4 as explained before, the carry-forward may be administered as next following administration (step S50).

In a further variant, steps S51, S52 may be carried out before step S50 and the refilling threshold in step S51 may optionally be variable and correspond to the amount that shall subsequently be administered in step S50. For this type of embodiment, it is ensured that an administration step (S50) can be carried out without requiring refilling in-between.

Furthermore, checking the state of the dosing unit (step S51) may be carried out continuously and/or during step S50.

Furthermore, step S52 may be modified to allow refilling of the dosing cylinder 300 from the container 5 even if the remaining filling amount is not sufficient for a full filling. In this case, step S2 may be modified such that the distance by which the piston is moved into the retraction direction, is limited such that the amount of liquid drug that is sucked into the dosing cylinder 300 corresponds to the remaining filling volume of the container 5 as determined in preceding step S52, potentially including a safety margin of remaining liquid in the container 5. Further variants and aspects of (re-)filling and dosing strategies that may be used in the present context are disclosed in the WO2012/140063.

As explained before, step S3 involves displacing liquid drug out the dosing cylinder 300 back into the container 5. In this context, it is particularly favorable if the container 5 is realized as a flexible or semi-flexible container, e.g., according to the disclosure of WO2012/065780. A flexible or semi-flexible container has the advantage that substantially no liquid pressure/force is required in order to increase or decrease its inner volume. Alternatively, however, the container 5 may also be a cartridge with a sealing and displaceable cartridge piston as largely known from standard syringe-driver infusion systems. In this case, the friction of the cartridge piston needs to be sufficiently small to allow displacement of the cartridge piston via the fluidic pushing, respectively suction, pressure that occurs when forcing liquid into, respectively sucking liquid out of, the cartridge via the dosing unit 3.

The ambulatory infusion device may include sensors that measure the filling level of the container 5 and/or of the dosing cylinder 300, the latter, e.g., via detecting the displacement position of the piston 302, e.g., according to WO2012/140052. Alternatively, the filling volume of the container 5 and in particular of the dosing cylinder 300 which is used in steps S51, S52 may be determined computationally by increasing, respectively decreasing, a corresponding volume counter in accordance with the piston displacement and the corresponding liquid volume change in the dosing cylinder 300. Assuming the retracted, respectively advanced, piston stop position may, e.g., be determined via a monitoring operation of the pump actuator 20 since the piston 302 cannot be further displaced in the end positions, resulting in the pump actuator tending to stall. This may be detected, e.g., by monitoring a motor current and/or a evaluating an encoder signal, e.g., of an incremental rotational encoder on the motor shaft. An encoder as part of the pump actuator 20 may further be favorably used for monitoring the operation of the pump drive unit 2, in particular during administration to the patient (step S50). It is noted that a monitoring at the pump actuator 20 has some inherent imprecision because of the backlash. This, however, is uncritical because subsequent to the (re)filling of the dosing cylinder 300, the backlash is compensated for in step S3 before administrations to the patient are carried out in step S50.

While this invention has been described as having an exemplary design, the present invention may be further modified within the spirit and scope of this disclosure. This application is therefore intended to cover any variations, uses, or adaptations of the invention using its general principles.

What is claimed is:

1. Ambulatory infusion device for use with a valve unit and a metering pump unit having a piston, the ambulatory infusion device including:
    a pump drive unit including a pump actuator and a pump driver, the pump driver being coupled to the pump actuator and being coupleable to the piston of the metering pump unit to thereby transmit a pump driving force and/or pump driving torque from the pump actuator to the piston;
    a valve drive unit including a valve actuator and a valve driver, the valve driver being coupled to the valve actuator and being coupleable to the valve unit to thereby transmit a valve switching force and/or valve switching torque from the valve actuator to the valve unit;
    a control unit being configured to control a repeated execution of a sequence of steps after priming a fluidic system extending from a drug reservoir through the metering pump unit to an infusion site, wherein each of the following steps is executed in each repetition of the sequence of steps:
        (a) operating the valve actuator to switch the valve unit to a filling state;
        (b) operating the pump actuator to move the piston in a retraction direction to a retracted piston stop position;
        (c) operating the pump actuator to move the piston a predefined backlash compensation distance in an advancing direction with the valve unit in the filling state, the advancing direction being opposite to the retraction direction;
        (d) operating the valve actuator to switch the valve unit from the filling state to a draining state;
        (e) operating the pump actuator to further move the piston in the advancing direction in a plurality of incremental steps over an extended time period no further than an advanced piston stop position; and
    wherein neither the retracted piston stop position nor the advanced piston stop position are defined by a mechanical stop.

2. Ambulatory infusion device according to claim 1 wherein the backlash compensation distance is between 0.3 mm and 1 mm.

3. Ambulatory infusion device according to claim 1 wherein the control unit is configured to start a sequence of step (a) to (e) in the advanced piston stop position.

4. Ambulatory infusion device according to claim 1 wherein the control unit is configured, in step (b), to stop operating the pump actuator upon the piston assuming the retracted piston stop position.

5. Ambulatory infusion device according to claim 1 wherein the pump drive unit is a rotatory drive or a linear displacement drive.

6. Ambulatory infusion device according to claim 1 wherein the valve driver includes a meshing pin for meshing engagement with a valve driver coupler of the valve unit.

7. Ambulatory infusion device according to claim 1 wherein the valve driver is a driver element of a step switching mechanism and is formed by a Geneva wheel mechanism.

8. Ambulatory infusion device according to claim 1 wherein the valve actuator includes either a stepper motor or a Shape Memory Alloy (SMA) actuator.

9. Ambulatory infusion device according to claim 1 wherein the control unit is configured to detect if the piston is in the retracted piston stop position or the advanced piston stop position.

10. Ambulatory infusion device according to claim 1 wherein the ambulatory infusion device is designed for releasable coupling with a dosing unit via a coupling movement wherein the dosing unit includes the metering pump unit and the valve unit.

11. Ambulatory infusion device according to claim 10 wherein the valve drive unit is disengaged from the valve unit during the coupling movement.

12. Ambulatory infusion system, including:
an ambulatory infusion device according to claim 1 and a dosing unit wherein the dosing unit includes:
the metering pump unit, the metering pump unit including a dosing cylinder and the piston, the piston being arranged inside the dosing cylinder in a sealing manner and being moveable between the retracted piston stop position and the advanced piston stop position;
the valve unit having a filling port, a draining port, and a shut-off body, the filling port being fluidically coupleable with the drug reservoir, the draining port being fluidically coupleable with an infusion site interface, the shut-off body defining a flow channel arrangement and being movable between a filling position where the flow channel arrangement fluidically couples the filling port with the dosing cylinder and fluidically isolates the draining port from the flow channel arrangement of the shut-off body, and a draining position where the flow channel arrangement fluidically couples the dosing cylinder with the draining port and fluidically isolates the filling port from the flow channel arrangement of the shut-off body;
a pump driver coupler, the pump driver coupler being coupled to or integral with the piston;
a valve driver coupler, the valve driver coupler being coupled to or integral with the shut-off body; and
wherein the valve driver is in engagement with the valve driver coupler and the pump driver is in engagement with the pump driver coupler.

13. Ambulatory infusion device according to claim 1 wherein the predefined backlash compensation distance is equivalent to the sum of a backlash distance resulting from drive chain tolerances and a safety margin.

14. A method of compensating for backlash in a dosing unit for liquid drug infusion, the method including disposing the dosing unit in a fluidic system extending from a drug reservoir through the dosing unit to an infusion site and priming the fluidic system and, subsequent to priming the fluidic system, repeatedly executing a sequence of steps wherein each of the following steps is executed in each repetition of the sequence of steps:
(a) switching a valve unit into a filling state;
(b) moving a piston in a retraction direction into a retracted piston stop position wherein the retracted piston stop position is not defined by a mechanical stop;
(c) moving the piston by a predefined backlash compensation distance in an advancing direction with the valve unit in the filling state, the advancing direction being opposite to the retraction direction;
(d) switching the valve unit from the filling state into a draining state;
(e) further moving the piston in the advancing direction in a plurality of incremental steps over an extended time period to an advanced piston stop position wherein the advanced piston stop position is not defined by a mechanical stop.

15. The method according to claim 14 wherein the piston is disposed in a dosing cylinder and steps (b) and (c) are performed while the dosing cylinder is fluidically coupled with a container containing a liquid drug and wherein a quantity of the liquid drug enters the dosing cylinder during step (b) and a portion of the quantity of the liquid drug is expelled from the dosing cylinder back into the container during step (c).

16. The method according to claim 14 wherein the predefined backlash compensation distance is equivalent to the sum of a backlash distance resulting from drive chain tolerances and a safety margin.

* * * * *